(12) United States Patent
Oster et al.

(10) Patent No.: US 8,262,629 B2
(45) Date of Patent: Sep. 11, 2012

(54) CATHETER PORT

(75) Inventors: Marcel Oster, Mönchengladbach (DE); Rainer Schumacher, Taunusstein (DE)

(73) Assignee: Fresenius Kabi Deutschland GmbH, Bad Homburg (DE)

(*) Notice: Subject to any disclaimer, the term of this patent is extended or adjusted under 35 U.S.C. 154(b) by 279 days.

(21) Appl. No.: 12/444,171

(22) PCT Filed: Oct. 4, 2007

(86) PCT No.: PCT/EP2007/008598
§ 371 (c)(1),
(2), (4) Date: Apr. 3, 2009

(87) PCT Pub. No.: WO2008/040538
PCT Pub. Date: Apr. 10, 2008

(65) Prior Publication Data
US 2010/0042073 A1  Feb. 18, 2010

(30) Foreign Application Priority Data
Oct. 7, 2006  (DE) .......................... 10 2006 047 519

(51) Int. Cl.
*A61M 37/00* (2006.01)

(52) U.S. Cl. ......... 604/288.01; 604/288.02; 604/288.03; 604/288.04

(58) Field of Classification Search .................. 604/175, 604/283, 539, 890.1, 288.01, 288.02, 288.03, 604/288.04
See application file for complete search history.

(56) References Cited

U.S. PATENT DOCUMENTS

| | | | |
|---|---|---|---|
| 4,772,270 A | 9/1988 | Wiita et al. | |
| 5,213,574 A | 5/1993 | Tucker | |
| 5,318,545 A | 6/1994 | Tucker | |
| 5,460,612 A | 10/1995 | Madore | |
| 5,718,682 A | 2/1998 | Tucker | |
| 6,213,973 B1 * | 4/2001 | Eliasen et al. | ............. 604/93.01 |
| 2004/0204692 A1 * | 10/2004 | Eliasen | .................... 604/288.02 |
| 2007/0123831 A1 | 5/2007 | Haindl et al. | |

FOREIGN PATENT DOCUMENTS

| | | |
|---|---|---|
| DE | 4129782 C1 | 9/1991 |
| EP | 0619101 A1 | 10/1994 |
| WO | WO 01/60444 A1 | 8/2001 |

* cited by examiner

*Primary Examiner* — Kevin C Sirmons
*Assistant Examiner* — Imani Hayman
(74) *Attorney, Agent, or Firm* — Occhiuti Rohlicek & Tsao LLP

(57) ABSTRACT

The invention relates to a catheter port for supplying an active substance to an active site which is distant from the port. According to the invention, the housing (1) of the port is designed to have two parts, an upper housing part (7) and a lower housing part (6). The upper housing part (7) holds an insertion part (10) in a clamping manner in a housing recess (8) of the lower housing part (6), wherein a chamber (11) is arranged in said insertion part for receiving the active substance with the interpositioning of a punctured membrane (17) that can be pierced with an injection cannula. While the insertion part (10) and the chamber (11) can be manufactured from a material resistant to the active substance, preferably a heavier ceramics, the upper and lower housing parts may consist of a lighter biocompatible plastic material. It is advantageous that the patient only comes into contact with the upper and lower housing parts made of a biocompatible plastic material and not with the insertion part.

25 Claims, 3 Drawing Sheets

CATHETER PORT

Figure 1:
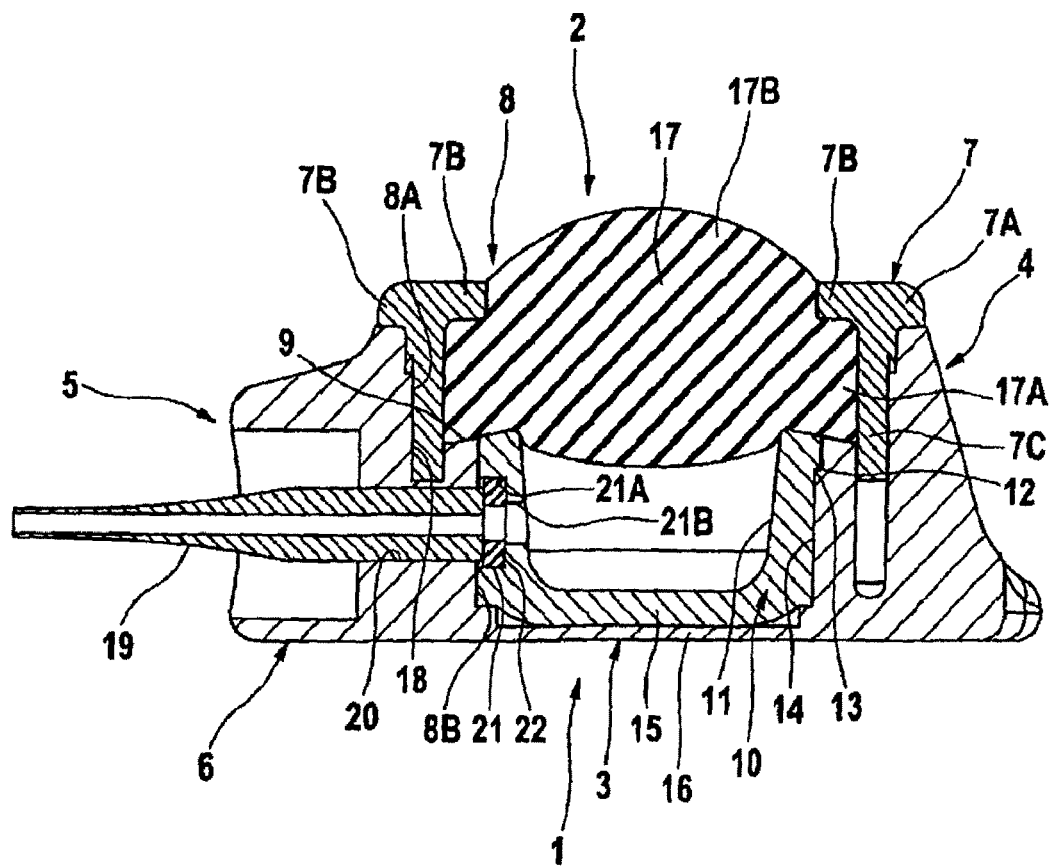

The invention relates to a catheter port for the administration of an active substance to a remote active site.

For the administration of active substances, it is known to implant a port under the patient's skin, there being connected to said port a catheter which leads to the active site at which the active substance is intended to arrive. The port comprises a chamber for accommodating the active substance, said chamber being sealed by a pierceable membrane which lies beneath the skin. For the filling of the chamber, the skin and the membrane lying beneath are punctured by a cannula and the active substance is injected into the chamber. The active substance then passes from the chamber via the catheter to the active site.

DE 41 29 782 C1 describes a port which comprises a housing with a lower recess for accommodating the active substance and an upper recess for accommodating the membrane. The membrane is held in the recess by means of a clamping ring which exerts a pressure on the membrane, so that the membrane arches outwards.

There is known from U.S. Pat. No. 5,718,682 a port, the housing whereof comprises an upper and a lower part, which are screwed together with the interposition of a membrane. The chamber for accommodating the active substance is formed in the lower housing part, whilst the upper housing part serves as a clamping ring.

U.S. Pat. No. 4,772,270 also describes a port with a two-part housing, the lower housing part whereof being constituted as a chamber. The membrane is clamped between the upper housing part and lower housing part.

With the known port systems, the problem arises that the housing part for accommodating the active substance has to be produced from a material resistant to the active substance, whilst the housing part which comes into contact with the patient has to be made from a biocompatible material. Overall, the port should have a low weight and be insensitive to impacts and knocks. In particular, the chamber for accommodating the active substance should not be able to be damaged by a slipping cannula.

U.S. Pat. No. 6,213,973 proposes producing all the housing parts from a biocompatible plastic or from another biocompatible material, for example metal or ceramic, which cannot be damaged by the needle used to fill the port. However, the publication also proposes, as an alternative, producing the housing parts from different materials.

WO 05/032645 describes a port system with an implantable port and a catheter, wherein the chamber for accommodating the active substance is formed in an insertion part, which is locked in a recess of a one-part housing body with the clamped interposition of the membrane, in such a way that the insertion part exerts a contact pressure on the membrane. The insertion part and the housing are constituted as a bayonet lock, so that the insertion part is easily inserted into the housing and is fixed securely in the housing after closure of the bayonet lock. The insertion part sits in the housing recess in such a way that its underside terminates flush with the housing underside.

The advantage of the port system known from WO/05032645, which comprises an active substance chamber, lies in the fact that the insertion part can be produced from a material different from the port housing, for example plastic or metal, in particular titanium or ceramic, without the whole port having to be changed. A drawback, however, is the relatively expensive bayonet lock.

The problem underlying the invention is to provide a catheter port which is easy to assemble and permits the parts coming into contact with the active substance to be produced from a material resistant to the active substance, in particular ceramic or metal, whilst the parts coming into contact with the patient can be made of a biocompatible material.

According to the invention, the solution to this problem takes place with the features of claim 1. Preferred embodiments of the invention are the subject-matter of the sub-claims.

The port according to the invention comprises a two-part housing, into which an insertion part is inserted, in which a chamber for accommodating an active substance is formed.

The insertion part is held by the upper housing part with the interposition of a self-sealing membrane (septum) in a clamped manner in a housing recess of the lower housing part. The insertion part is completely shielded from the exterior by the housing parts and the membrane. The insertion part does not have any contact area at the outer enveloping surface of the port.

The upper housing part and lower housing part coming into contact with the patient can be produced from a lighter biocompatible material, whilst the insertion part can be made, independently of the upper housing part and lower housing part, from a material resistant to the active substance, but possibly a heavier one. Although the parts coming into contact with the patient and the parts of the port coming into contact with the active substance can be produced from different materials, the assembly of the parts of the port made of different materials is straightforward, because for the assembly it is merely necessary to insert the insertion part into the housing recess of the lower housing part and to connect the upper housing part and lower housing part together with the interposition of the membrane, as a result of which the insertion part is held in a clamped manner in the housing recess.

In a preferred embodiment of the port according to the invention, the upper housing part and lower housing part are made of a biocompatible plastic. Such plastics are known to the person skilled in the art, a preferred plastic being for example PEEK. They are characterised not only by biocompatibility, but also by a lower weight compared to metal or ceramic. Moreover, the upper housing part and lower housing part can be produced in a straightforward manner in the injection moulding process and with unrestricted shaping, which would not be the case with metal or ceramic housings.

The insertion part with the chamber for accommodating the active substance, on the other hand, is preferably made from a ceramic or metallic material, preference being given to a ceramic material. Such materials are known to the person skilled in the art. They are characterised by the fact that they are basically resistant to the active substances and cannot be pierced by the cannula.

The decisive advantage of the port according to the invention lies in the fact that the insertion part with the chamber for accommodating the active substance, which can be made from a different material than the housing, is completely surrounded by the housing and the membrane, so that the insertion part does not come into contact with the patient.

A further preferred embodiment of the invention makes provision such that the upper housing part and lower housing part are welded together. The two housing parts are preferably connected to one another rigidly in the ultrasound welding process. A reliable and reproducible connection is thus obtained, the process data of the welding process being able to be readily documented for each port. A closed sealed system without adhesive joints is created.

In a further preferred embodiment, the upper housing part is inserted into the housing recess of the lower housing part. The upper housing part is thus surrounded by the lower housing part. This is advantageous, inasmuch as the membrane received by the upper housing part and lower housing part as a result of the design can easily be inserted without there being a risk of the membrane being pinched by the housing parts to be connected. It is however also possible in principle for the upper housing part to be placed onto the lower housing part and to surround the lower housing part.

In a further preferred embodiment, the upper housing part comprises a lower and an upper section, the lower section surrounding the membrane in an annular manner and preferably extending into a groove of the lower housing part, whilst the upper section on the one hand engages over the membrane and on the other hand rests on the lower housing part.

Since the lower section of the upper housing part preferably extending into a groove of the lower housing part does not rest on the lower housing part, it is ensured even with relatively large manufacturing tolerances that the upper section of the upper housing part lies firmly on the lower housing part thereby pressing on the membrane.

A further preferred embodiment makes provision such that the insertion part comprises a flange, with which the insertion part rests on a shoulder in the housing recess of the lower housing part. The effect of this is that the insertion part can rest on the lower housing part in a region in which the lower housing part can be designed to be particularly thick-walled and stable.

The insertion part is preferably an essentially hollow-cylindrical body which is closed at the underside by a base part, whilst the housing recess of the lower housing part is preferably designed essentially cylindrical. It is however also possible for the insertion part and housing recess not to have an essentially circular cross-section, but rather an elliptical or rectangular cross-section. The essentially rotationally symmetrical design does however have advantages in production and handling.

In a further preferred embodiment, the insertion part is inserted into the lower housing part in a torsion-resistant manner. For this purpose, the insertion part preferably comprises an outwardly projecting shoulder which, when the insertion part is inserted into the housing recess, engages in a corresponding recess of the lower housing part. The projecting shoulder of the insertion part can for example have a rectangular cross-section, which is pushed into an upwardly open groove of the lower housing part. The insertion part can be inserted into the lower housing part in an easily assemblable and torsion-resistant manner.

For the connection of the catheter to the port according to the invention, a connection piece is preferably provided which is preferably designed as a cannula extending through a hole of the lower housing part.

For the purpose of sealing the cannula with respect to the lower housing part, a further preferred embodiment provides a sealing ring, preferably a silicone sealing ring, which sits on the cannula and lies in a recess of the insertion part. The cannula is preferably glued and/or welded to the remaining parts of the port. No particular requirements are however made on the gluing or welding of the cannula, since the sealing ring takes over the sealing function.

An example of embodiment of the port according to the invention is explained in greater detail below by reference to the drawings.

Figure 2:
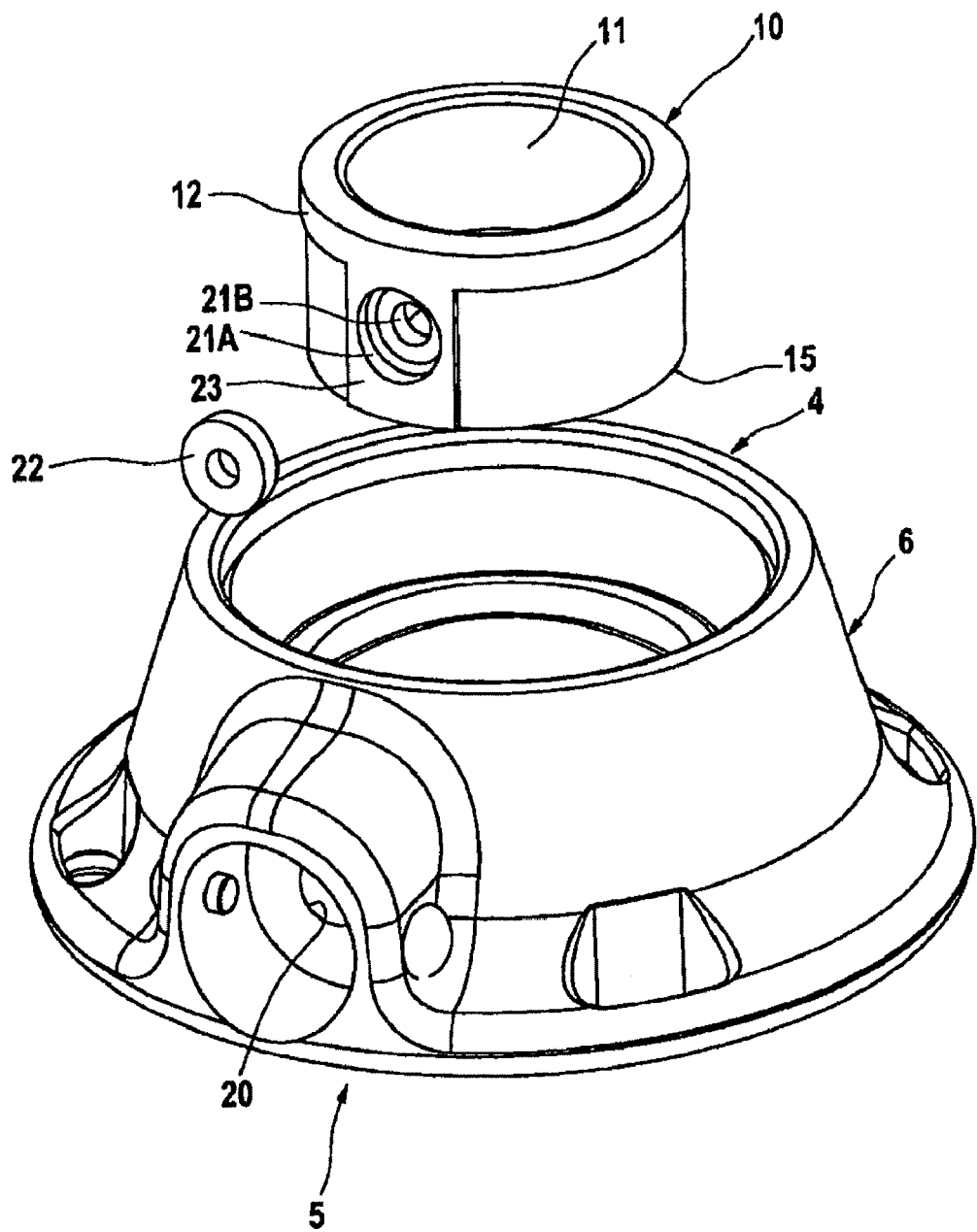
Figure 3:
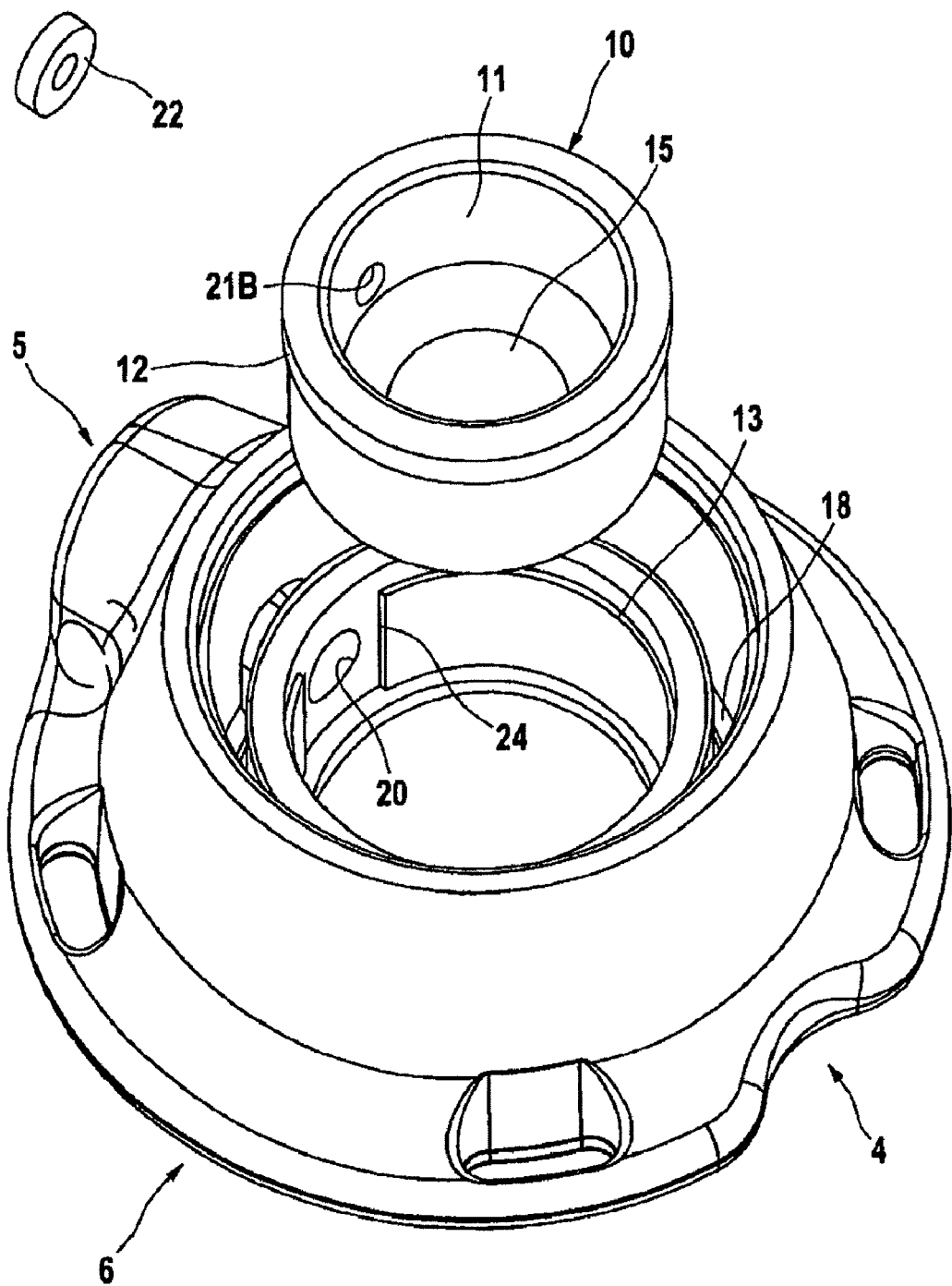

In the drawings:

FIG. 1 shows the port according to the invention in a cross-sectional representation, FIG. 2 shows a perspective exploded representation of the lower housing part and the insertion part of the port according to the invention in a view from the side and FIG. 3 shows a perspective exploded representation of the lower housing part and the insertion part of the port according to the invention in a view from above.

FIG. 1 shows the port according to the invention in a cross-sectional representation, whilst FIGS. 2 and 3 show an exploded representation of the lower housing part and the insertion part in a magnified representation. The port, which can have roughly the size of a finger-tip, comprises a flat housing 1, which is implanted under the patient's skin. The upper side of port housing 1 lying under the skin is designated by reference number 2, the underside of the housing by 3, the housing front side by 4 and the housing rear side by 5.

Housing 1 is constituted in two parts. It comprises a lower housing part 6 and an upper housing part 7. Upper housing part and lower housing part 6, 7 are injection moulded parts made from a biocompatible plastic.

Lower housing part 6 comprises a central, upwardly open recess 8, which has an upper region 8A with a larger diameter and a lower region 8B with a smaller diameter thereby forming a step 9. Inserted in a mating manner into lower region 8B of recess 8 is an essentially cylindrical insertion part 10, in which an upwardly open chamber 11 for accommodating the liquid active substance is formed. The upper side of insertion part 10 terminates flush with slightly inclined, inwardly running step 9.

Insertion part 10 is an essentially hollow-cylindrical body, which is closed at the underside by a base part 15. It is made from a metallic or ceramic material, preferably a ceramic, which is resistant to the active substance. Insertion part 10 comprises at its upper edge a flange 12, with which the insertion part rests on a shoulder 13 which is formed at wall 14 of lower region 8B of recess 8. A certain degree of play is present between base part 15 of the insertion part and housing base 16, so that insertion part 10 rests not on the housing base, but with flange 12 on lower housing part 6 in the region in which the lower housing part is designed thick-walled. The housing base is thus relieved of the load.

A self-sealing membrane 17 made from a biocompatible material and pierceable with an injection cannula sits in housing recess 8 above insertion part 10. Upper housing part 7 holds membrane 17 together with insertion part 10 firmly in housing recess 8, the insertion part being inserted in a mating manner into upper region 8A of housing recess 8. Membrane 17 exerts from above a contact pressure on the upper side of insertion part 10, so that the insertion part sits firmly in lower region 8B of housing recess 8.

Upper housing part 7 comprises an outwardly pointing upper region 7A, with which upper housing part 7 rests on the upper side of lower housing part 6 in the edge region of housing recess 8. With an inwardly pointing upper section 7B, upper housing part 7 engages over the edge region of membrane 17, so that the membrane is pressed against step 9 of lower housing part 6 and the upper side of insertion part 11.

Moreover, upper housing part 7 comprises a lower section 7C surrounding the membrane in an annular manner, said section sitting in a mating manner in upper region 8B of housing recess 8. Lower region 7C of upper housing part 7 extends into an annular groove 18, which is formed in lower housing part 6.

Membrane 17 comprises an essentially cylindrical lower region 17A surrounded by upper housing part 7 and an upper spherical-cap-shaped region 17B produced by tension, which arches outwards and lies free and is surrounded by upper housing part 7 in an annular manner.

Upper housing part 7 and lower housing part 6 are welded together after the insertion of insertion part 10 and membrane 17, preferably using an ultrasound welding process. The design-related accommodation of membrane 17 by upper housing part and lower housing part 7, 6 prevents the membrane from being pinched by the parts to be welded during assembly. Before assembly, the components made of PEEK are heated up according to a prescribed cycle in order to obtain the optimum crystallisation state. The open chamber (11) thus has no common contact area with the housing parts (7, 6).

For the connection of a catheter not represented in the figures, the port comprises a connection piece 19 which is formed as a cannula. Cannula 19 sits in a transversely running hole 20 at rear side 5 of lower housing part 6 and extends up to a hole 21 aligned therewith in insertion part 10. Hole 21 of insertion part 11 comprises an outer section 21A with a larger diameter and an inner section 21B with a smaller diameter. The diameter of outer section 21A is dimensioned in such a way that a sealing ring, preferably a silicone sealing ring 22, can be inserted in a mating manner into the hole, whilst the diameter of inner section 21B is smaller than the diameter of sealing ring 22 and cannula 19. Sealing ring 22 sitting on the inner end piece of cannula 19, which sealing ring sits in outer section 21A of hole 21, seals cannula 19 with respect to insertion part 10. When use is made in the intended manner, an administered active substance thus comes into contact only with resistant materials. The cannula 19 is also glued to lower housing part 20, the gluing creating an additional seal. The outwardly projecting section of cannula 19 can have various geometries, so that the known catheters not represented in the figures can be pushed onto the cannula. A possible embodiment of the cannula is a tapering, trumpet-like shape.

At the side facing rear side 5 of lower housing part 6, insertion part 10 comprises an outwardly projecting shoulder 23 with a rectangular cross-section, which extends from the base of the insertion part up to the underside of flange 12. Outwardly projecting shoulder 23 sits in a recess 24, which is formed in the wall of lower section 8B of housing opening 8 in the region of hole 20 and is open towards step 9. It is thus possible to push insertion part 10 with projecting shoulder 23 from above into groove 24. Shoulder 23 of insertion part 10 sitting in a mating manner in groove 24 firmly holds the insertion part in a rotation-resistant manner in housing recess 8.

For the purpose of filling the port, membrane 17 is pierced with an injection cannula, and a liquid active substance is injected into chamber 11 of insertion part 10. The active substance then passes through hole 21 in insertion part 10 and cannula 19 via the catheter (not shown) to the active site which is remote from the port.

The invention claimed is:

1. A catheter port comprising
a housing which comprises a recess,
an insertion part which is disposed in the housing recess and in which a chamber for accommodating an active substance is formed,
a membrane disposed above the chamber in the housing recess, and
a connection piece for a catheter, said connection piece being in a fluid connection with the chamber,
wherein the housing is constituted in two parts comprising an upper housing part and a lower housing part,
the insertion part comprises an outwardly projecting shoulder which, when the insertion part is inserted into the housing recess, engages the lower housing part in a torsion-resistant manner,
the insertion part is held by the upper housing part with the interposition of the membrane in a clamped manner in a housing recess of the lower housing part,
the housing further comprises a housing sidewall including an opening configured to receive the connection piece, and a housing base that closes an end of the housing sidewall, the housing base and housing sidewall defining the housing recess, and
the outwardly projecting shoulder of the insertion part engages a corresponding recess formed in an inward-facing surface of the housing recess to provide the torsion-resistant engagement between the insertion art and the lower housing part.

2. The port according to claim 1, wherein the upper housing part and the lower housing part are made from a material different from the insertion part.

3. The port according to claim 1, the upper housing part and the lower housing part are made from a biocompatible plastic.

4. The port according to claim 1, wherein the insertion part is made from a ceramic material or from a metallic material.

5. The port according to claim 1, wherein the upper housing part and the lower housing part are welded together.

6. The port according to claim 1, wherein the upper housing part is inserted into the housing recess of the lower housing part.

7. The port according to claim 1, wherein the upper housing part comprises a lower section surrounding the membrane in an annular manner.

8. The port according to claim 7, wherein the lower section of the upper housing part surrounding the membrane in an annular manner extends into a groove of the lower housing part.

9. The port according to claim 1, wherein the upper housing part comprises an upper section engaging over the membrane.

10. The port according to claim 1, wherein the upper housing part comprises an upper section resting on the lower housing part.

11. The port according to claim 1, wherein the insertion part comprises a flange, with which the insertion part lies on a shoulder in the housing recess of the lower housing part.

12. The port according to claim 1, wherein the insertion part is an essentially hollow-cylindrical body, which is closed at the underside with a base part, and the housing recess of the lower housing part is formed essentially cylindrical.

13. The port according to claim 1, wherein the membrane comprises an essentially cylindrical lower section, which is surrounded in an annular manner by the upper housing part, and an essentially spherical-cap-shaped upper section which lies free.

14. The port according to claim 1, wherein the outwardly projecting shoulder engages a recess of the lower housing part.

15. The port according to claim 1, wherein the lower housing part comprises a hole, the connection piece for the catheter being designed as a cannula extending through the hole of the lower housing part.

16. The port according to claim 15, wherein the cannula is sealed with respect to the lower housing part by a sealing ring which sits on the cannula and which lies in a recess of the insertion part.

17. The port according to claim 1, wherein the insertion part does not have any contact area at the outer enveloping surface of the port.

18. The port according to claim 1, wherein the open chamber for accommodating the active substance does not have any common contact area with the upper housing part or the lower housing part.

19. The port according to claim 1, wherein the lower housing part comprises a hole and the insertion part comprises a hole aligned with the hole in the lower housing part.

20. The port according to claim 1, wherein
the housing further comprises a housing sidewall, and a housing base that closes a lower end of the housing sidewall, the housing base and housing sidewall defining the housing recess, and
the insertion part further comprises a flange that engages a corresponding shoulder formed in a surface of the housing recess, and the insertion part is supported within the housing recess by the flange such that the insertion part does not rest on the housing base.

21. A catheter port comprising:
a housing that is defined in part by a housing base, a generally continuous housing sidewall, a housing inlet opening disposed opposite the housing base, and a housing outlet opening disposed within the generally continuous housing sidewall;
a fluid-holding receptacle, separate and distinct from the housing, that is defined in part by a receptacle base, a generally continuous receptacle sidewall, a receptacle inlet opening disposed opposite the receptacle base, and a receptacle outlet opening disposed within the generally continuous receptacle sidewall, the receptacle being disposed within a recess of the housing such that a non-planar exterior profile of the generally continuous receptacle sidewall engages a non-planar interior profile of the generally continuous housing sidewall to align the receptacle outlet opening with the housing outlet opening; and
a membrane disposed within the recess of the housing in sealed engagement with the receptacle inlet opening, wherein
the exterior profile of the receptacle sidewall comprises a flange that engages a corresponding recess formed in the housing sidewall, and the receptacle is supported within the housing recess by the flange such that the receptacle does not rest on the housing base.

22. The catheter port of claim 21, wherein the housing includes an upper component and a lower component that together define the housing base and the generally continuous housing sidewall.

23. The catheter port of claim 21, wherein the housing and the receptacle are formed of different materials.

24. The catheter port of claim 21, wherein the recess of the housing has a substantially circular cross-section and the receptacle has a substantially circular cross-section, and wherein the receptacle is disposed within the recess of the housing such that the non-planar exterior profile of the generally continuous receptacle sidewall mates with the non-planar interior profile of the generally continuous housing sidewall to reduce rotational motion of the receptacle relative to the housing.

25. The port according to claim 21, wherein
the non-planar exterior profile of the generally continuous receptacle sidewall comprises a shoulder that projects outward from an outer surface of the receptacle sidewall, and the non-planar interior profile of the generally continuous housing sidewall comprises a recess, the shoulder engaging with the recess to align the receptacle outlet opening with the housing outlet opening.

* * * * *